United States Patent [19]

Wiegand

[11] 4,070,394
[45] Jan. 24, 1978

[54] CARNITINE NITRILE HALIDE PREPARATION

[75] Inventor: Karl E. Wiegand, Baton Rouge, La.

[73] Assignee: Ethyl Corporation, Richmond, Va.

[21] Appl. No.: 776,506

[22] Filed: Mar. 11, 1977

Related U.S. Application Data

[63] Continuation-in-part of Ser. No. 651,824, Jan. 23, 1976, abandoned.

[51] Int. Cl.$^2$ ............................................. C07C 120/00
[52] U.S. Cl. .............................................. 260/465.5 R
[58] Field of Search ................................. 260/465.5 R

[56] References Cited

U.S. PATENT DOCUMENTS

| | | | |
|---|---|---|---|
| 3,135,788 | 6/1964 | Noguchi et al. | 260/465.5 R X |
| 3,151,149 | 9/1964 | Strack et al. | 260/465.5 R |
| 3,488,379 | 1/1970 | Dohi et al. | 260/465.5 R X |

OTHER PUBLICATIONS

Migrdichian; The Chemistry of Organic Cyanogen Compounds, 1947, p. 182.
Braun, J.A.C.S., 52, 1930, pp. 3167–3176.
Rappoport; The Chemistry of the Cyano Group, 1970, p. 86.

*Primary Examiner*—Joseph Paul Brust
*Attorney, Agent, or Firm*—Donald L. Johnson; John F. Sieberth; James M. Pelton

[57] ABSTRACT

A process for the preparation of carnitine nitrile halides by reacting (2,3-epoxypropyl)trimethylammonium halide with a cyano compound selected from the group consisting of alkali metal cyanide and hydrocyanic acid at a temperature of from about −20° to about 120° C in aqueous liquid medium.

10 Claims, No Drawings

CARNITINE NITRILE HALIDE PREPARATION

CROSS REFERENCE TO RELATED APPLICATION

This application is a continuation-in-part of application Ser. No. 651,824, filed Jan. 23, 1976, now abandoned.

BACKGROUND OF THE INVENTION

This invention relates to a method for the preparation of DL-carnitine hydrochloride and in particular to a novel synthetic method for preparing DL-carnitine nitrile halide which is an intermediate for DL-carnitine hydrochloride.

The chemical nomenclature of said DL-carnitine hydrochloride is DL-gamma-trimethylammonium-beta-hydroxybutyrate hydrochloride and is represented by the following structural formula:

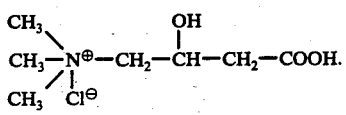

The carnitine nitrile halide is more properly referred to as DL-gamma-trimethylammonium-beta-hydroxybutyronitrile chloride and is represented by the following structural formula:

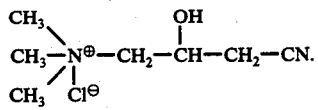

As used hereinbelow, the conventional designation of "carnitine" will be used in place of the rather lengthy designation DL-carnitine hydrochloride or its chemical name. Also, "carnitine nitrile halide" will be used herein instead of the lengthy designation or the chemical name of the intermediate for producing carnitine.

Carnitine is a substance that was found in the muscle extract of mammals by Gulevisch and Krimberg (Z. Physiol. Chem., 45, 326), and by Kutscher (Z. Untersuch. Nahr. u. Genussm., 10, 528) in 1905. The constitutional formula of carnitine was determined by Tomita and others in 1927. In 1952, carnitine was proved by Carter et al to be the same substance as vitamin $B_T$, a new member of the vitamin B group, which has been discovered by Fraenkel et al in 1948.

Numerous studies have been made on the physiological and pharmacological actions of Vitamin $B_T$, i.e., carnitine.

The preparative methods of carnitine may be divided into two classes, that is, an extracting process from natural materials and a chemical synthesis. A number of methods have been proposed up to the present. The extracting process from natural materials, however, does not go beyond the laboratory scale. On the other hand, the synthetic method, which is now considered to be successful to a certain extent, includes many difficulties, such as, an extremely low yield and a large amount of by-products. These difficulties make it practically impossible to obtain a product of high purity.

The method of Friedman [Biochem. Preparations, 6 (1958)] is an example of the extracting processes from natural sources. According to this method, carnitine is isolated from beef extract by treating with organic solvents, ion-exchange resins and other agents, but the yield of carnitine is only about 7 grams based on 450 grams of beef extract. The method devices by Carter and Bhattacharyya [J. Amer. Chem. Soc., 75, 2503 (1953)] is an example of the synthetic methods. According to this method, carnitine is to be synthesized from benzaldehyde and epichlorohydrin, through several steps. The final yield of carnitine is but ca. 20-25 percent. The method by Dechamps and others [Compt. rend., 283, 826 (1954)] is another example of a synthetic method, in which gamma-chloro-beta-hydroxybutyronitrile that has been preliminarily synthesized is made to react with trimethylamine, and the reaction product hydrolyzed under pressure to produce dicarnitine, but the yield is only ca. 20 percent.

More recently, Noguchi et al, U.S. Pat. No. 3,135,788, has substantially increased yields by reacting the halohydrin with trimethylamine hydrochloride to produce a 3-halo-2-hydroxypropyl trimethylammonium chloride which has been reacted with sodium or potassium cyanide to produce a 3-cyano-2-hydroxypropyl trimethylammonium chloride and alkali metal halide by-product, followed by hydrolysis to produce carnitine. Yields up to 85 percent in the crude product and about 75 percent in the refined product have been achieved. Also, (2,3-epoxypropyl)trimethylammonium chloride has been prepared in high yield and purity from epichlorohydrin and trimethylamine by reacting in an organic solvent, J. D. McClure, J. Org. Chem., 35, No. 6, 2059 (1970). Apparently, the use of an organic solvent rather than an aqueous liquid reaction medium preserves the epoxide ring rather than producing the 2-hydroxy-3-chloro compound, as occurs in Noguchi et al. It now has been found that the compound prepared by McClure can be employed in the synthetic preparation of carnitine nitrile chloride to achieve almost quantitative yield. Using this novel procedure as more fully described hereinbelow, the formation of water-soluble alkali metal halide is avoided. This is significant because the carnitine nitrile chloride is also water-soluble. Thus, avoiding the formation of alkali metal halide and its subsequent removal from the reactor and separation from the product, carnitine nitrile chloride results in a much cleaner product and quantitative yield.

THE INVENTION

I have now found that (2,3,-epoxypropyl)trimethylammonium halide can be reacted with a cyano compound selected from a metal cyanide, ammonium cyanide and hydrocyanic acid in a liquid aqueous medium to produce carnitine nitrile halide in almost quantitative yield and without the formation of by-product salts.

As a preferred embodiment of my invention there is provided a process for the production of carnitine nitrile halide without co-production of substantial amounts of water-soluble salts consisting of, in combination, the steps of (a) contacting 2,3-epoxypropyl halide with trimethylamine in an organic solvent to produce a 2,3-epoxypropyl trimethyl ammonium halide, (b) removing the organic solvent from said 2,3-epoxypropyl trimethyl ammonium halide, (c) mixing an inert liquid aqueous reaction medium with said 2,3-epoxypropyl trimethyl ammonium halide, and (d) contacting at a temperature from 0° to about 30° C, said 2,3-epoxypropyl trimethyl ammonium halide with a cyano compound selected from the group consisting of a metal cyanide, ammonium cyanide and hydrocyanic acid whereby carnitine nitrile halide is produced without co-production of substantial amounts of water soluble salts.

As mentioned hereinabove, (2,3-epoxypropyl)trimethylammonium halide which is useful in the process of my invention can be prepared according to the method of McClure, supra, which is incorporated herein by reference as if fully set forth. Although this method speaks only of the chloride, it is clear that both the bromide and iodide can be prepared by using epibromohydrin or epiiodohydrin in the process of this invention.

According to my invention an epihalohydrin, such as epibromo- or epichlorohydrin, is reacted with an amine, such as a tertiary amine and, preferably, a tertiary aliphatic amine in an aprotic solvent to produce (2,3-epoxypropyl)trialkylammonium halide. Typical of the tertiary alphatic amines which can react in the process of my invention are triethyl amine, tripropyl amine, tributyl amine, tripentyl amine, trihexyl amine and the like. Even though these typical amines react according to the process of my invention, they do not produce carnitine nitrile halide, and so an especially preferred amine is trimethyl amine.

The preparation of (2,3-epoxypropyl)trialkylammonium halide is carried out in an organic solvent. Preferably, the solvent is an aprotic solvent. Many aprotic solvents are known and useful in the process of my invention. Typical examples of the solvent are acetone, tetrahydrofuran, dimethoxyethane, ether, ethyl acetate and the like. It is more preferable that the intermediate (2,3-epoxypropyl)trialkylammonium halide produced in this step of the process is insoluble in the aprotic solvent and on formation precipitates from the solution. A most preferred organic aprotic solvent which meets the criteria of insolubility of product therein is an excess of the epihalohydrin reactant. Preferably, a large excess is employed, such as from four to about seven fold greater on a weight basis than the trialkyl amine employed. Thus, in a more highly preferred embodiment of my invention, a 2,3-epoxypropyl halide is contacted with trimethyl amine in an inert organic solvent, more preferably an aprotic solvent, and most preferably an excess of the epoxy compound, to produce a 2,3-epoxypropyl trimethyl ammonium halide which precipitates from solution as it forms, followed by removal of the solvent from the 2,3-epoxypropyl trimethyl ammonium halide which is then used to form the carnitine nitrile halide.

The (2,3-epoxypropyl)trimethylammonium halide, preferably the chloride, is reacted with a cyano compound to produce carnitine nitrile halide, preferably the chloride. The cyano compound is one which is capable of donating a cyano or nitrile group to the (2,3-epoxypropyl)trimethylammonium halide. Thus, any nitrile compound which does not adversely affect the reaction can be employed. Typical of these are metal cyanides, ammonium cyanides and substituted ammonium cyanides. Also, adducts of aldehydes or ketones with hydrocyanic acid can be employed. Of course, hydrocyanic acid itself is a preferred source of cyano or nitrile groups. Typical of the metal cyanides are alkali and alkaline earth metal cyanides such as sodium, potassium, rubidium, calcium, strontium, barium and the like. Also transition metal cyanides such as ferrous and ferric cyanide, cadmium cyanide, lead cyanide, silver cyanide and the like can be employed. In addition to the simple cyanide compounds described above, a cyano compound in the form of complex addition salts, such as, gallium ferrocyanide, magnesium ferrocyanide, manganese cuprous cyanide, tin zinc cyanide and other well known complexes of metal cyanides can be employed in the process of this invention. Of the foregoing cyano compounds, the process of the present invention is preferably conducted using a cyano compound selected from the group consisting of an alkali metal cyanide and hydrocyanic acid because such materials are inexpensive, readily available and provide good yields of carnitine nitrile halides. Most preferred, of course, are sodium cyanide, potassium cyanide, rubidium cyanide and cesium cyanide for the alkali metal cyanides. In some cases, it is desirable to use hydrocyanic acid catalyzed with a small amount of the alkali metal cyanide. For such cases, only a very small amount of the alkali metal cyanide catalyst is required; that is to say, only an amount sufficient to initiate the reaction is used, after which the hydrocyanic acid reacts readily. Although the cyano compound described hereinabove reacts on an equimolar basis with (2,3-epoxypropyl)trimethylammonium chloride, a slight excess may be preferred in order to assure complete reaction of the (2,3-epoxypropyl)trimethylammonium halide.

A particular advantage of my process over the prior art processes is that by contacting the epoxide ring, instead of a 3-halo-2-hydroxypropyl group, with the cyano group no water soluble salts, for example NaCl, are formed. Others working in this area, as described in the "Background of the Invention" produce the water soluble salt which is more difficult to remove from the likewise water soluble carnitine nitrile halide product.

The reaction can be facilitated by conducting the reaction in the presence of a liquid reaction medium. In general, it is preferred that the liquid reaction medium be substantially inert to the reactants. Another function of the liquid reaction medium is to provide a substance for subsequent reaction with the cationic portion of the cyano compound. To illustrate this function of the liquid reaction medium in an aqueous liquid medium using sodium cyanide as a reactant, as the reaction proceeds, sodium hydroxide is produced as a by-product and the pH of the system will increase. Preferably, the liquid aqueous reaction medium is water. Although water itself is a preferred reaction medium, aqueous alcohol solutions can also be employed. Particularly when the alcohol is a lower alkanol, of which methanol, ethanol, propanol, isopropanol, butanol, sec-butanol and the like are typical, such aqueous alcohol solutions are suitable when a metal cyanide, such as alkali metal cyanide, is employed as the cyano compound. In the case of hydrocyanic acid, it is even possible to use neat alcohol, preferably lower alkanol, as the reaction medium. For the purposes of this invention the aqueous alcohol can be a solution or mixture of about 20 to 40 weight percent based on the starting (2,3-epoxypropyl)trimethylammonium halide. However, in general, only enough liquid aqueous reaction medium is required to facilitate mixing or stirring of the reactants. The specific amount is not critical and is governed only by good engineering practice with regard to sound principles of economics and practice.

The cyanation reaction is carried out at a temperature which is sufficient to initiate the reaction and give good reaction rates. A slightly elevated temperature is beneficial. Although the temperature is not critical, it has been found that temperatures from about −20° C to about 120° C can be satisfactory for good reaction rates. Preferably, a temperature of from about 0 to about 50° C is advantageous. Although higher temperatures have been used in the prior art, i.e, from about 30°–50° C or higher, it has been found that such temperatures are not required and can be avoided without detrimental affects on the reaction. Preferred temperatures range from 0° to 30° C.

The reaction proceeds until all of the reactants are consumed and the product carnitine nitrile halide is formed in good yield, preferably, the reaction occurs over a period of time sufficient to give good yield. Experience has shown that reaction times from about ½ hour to several days can be employed. Thus, the time does not appear critical so long as good contact of the reactants and sufficient temperatures are employed to obtain good yields.

Although not critical, the reaction is preferably conducted with slight agitation to facilitate the mixing of the reactants and heat transfer. Agitation can be carried out by conventional mixing, stirring or other agitating means well known to those skilled in the art.

Thus, in general the procedure employed in the present invention starts with 2,3-epoxypropyl halide, preferably the chloride, which is reacted with trimethylamine to produce (2,3-epoxypropyl)trimethylammonium chloride according to the method of McClure, as indicated hereinabove. The reaction medium of McClure can be removed and replaced with a liquid aqueous reaction medium and then the solution of (2,3-epoxypropyl)-trimethylammonium halide, preferably the chloride, can be mixed with alkali metal cyanide, preferably sodium cyanide, or hydrocyanic acid for reaction. In the case of hydrocyanic acid, a catalytic amount of an alkali metal cyanide can be added to initiate the reaction. Product recovery can be accomplished after reaction by decolorizing with charcoal, filtering the solution to remove solid materials, if any, and evaporating the liquid aqueous reaction medium or adding a concentrated mineral acid, particularly hydrochloric acid, to hydrolyze the nitrile group to the acid for the production of carnitine.

The following examples are given as illustration of the present process.

EXAMPLE 1

The method of McClure, supra, was followed on a reduced scale to produce (2,3-epoxypropyl)trimethylammonium chloride. To a suitable reaction vessel equipped with stirrer, gas addition tube and condenser cooled to −20 C was slowly added trimethylamine over a one hour period to a six-fold weight excess of epichlorohydrin maintained at −10° to 0° by external cooling. Stirring was continued for 5 hours at 20°–25° C. The crystals which separated were collected by filtration in a dry box and washed with ether several times. After drying in vacuo for one hour, the product analyzed by NMR was identified as (2,3-epoxypropyl)-trimethylammonium chloride. Yield of the reaction was about quantitative.

EXAMPLE 2

In a suitable reaction vessel, 1.5 g of (2,3-epoxypropyl)-trimethylammonium chloride from Example 1 was placed in 4 ml of water and mixed with 4.9 g of sodium cyanide in 4 ml of water at room temperature. The pH of the mixture increased from about 10.5 to about 12.9 over ½ hour with stirring, indicating the formation of sodium hydroxide. After 1 hour, PMR spectroscopy showed only carnitine nitrile chloride as determined by the absence of starting epoxide signals and complete superposition with added authentic carnitine nitrile chloride. The reaction was therefore essentially quantitative.

EXAMPLE 3

In a suitable reaction vessel, 3.5 ml of hydrocyanic acid, generated from 50 percent sulfuric acid action on sodium cyanide, was condensed into an ice bath receiver. Then, 1.1 g of (2,3-epoxypropyl)trimethylammonium chloride from Example 1 was dissolved in 4 ml of water and added to the receiver. The mixture was made up to 15 ml with water and a crystal of sodium cyanide was added. The mixture was allowed to come to room temperature and stand over 60 hours. After decolorization with charcoal, the filtered solution was concentrated under vacuum to about 4 ml and analyzed by PMR spectroscopy. The spectrum was completely superposable with added authentic carnitine nitrile chloride. Upon evaporation to dryness, the solids were identical with authentic carnitine nitrile chloride according to their infrared spectrum. Only trace impurities could be observed in this manner. Accordingly, the reaction appeared to be quantitative.

The reaction of (2,3-epoxypropyl)trimethylammonium bromide and iodide proceeds in essentially the same manner as the chloride illustrated above. Therefore, it is clear that the (2,3-epoxypropyl)trimethylammonium halide can be used in which the halide is selected from chloride, bromide or iodide. The chloride is preferred because of its ready preparation from epichlorohydrin as discussed hereinabove.

From the foregoing description of the process of this invention, which is only illustrative, it is clear that one skilled in the art can envision variations in the process which are nevertheless within the spirit of the invention. Therefore, it is desired that the process of this invention be limited only by the lawful scope of the following claims.

What is claimed is:

1. A process for the production of carnitine nitrile halide without co-production of substantial amounts of water-soluble salts consisting of, in combination, the steps of
   a. contacting a 2,3-epoxypropyl halide with trimethylamine in an organic solvent to produce a 2,3-epoxypropyl trimethyl ammonium halide,
   (b) removing the organic solvent from said 2,3-epoxypropyl trimethyl ammomium halide,
   (c) mixing an inert liquid aqueous reaction medium with said 2,3-epoxypropyl trimethyl ammonium halide, and
   (d) contacting at a temperature from 0° to about 30° C, said 2,3-epoxypropyl trimethyl ammonium halide with a cyano compound selected from the group consisting of a metal cyanide, ammonium cyanide and hydrocyanic acid whereby carnitine nitrile halide is produced without co-production of substantial amounts of water soluble salts.

2. The process of claim 1 wherein said halide is selected from chloride, bromide or iodide.

3. The process of claim 1 wherein said halide is chloride.

4. The process of claim 1 wherein said cyano compound is metal cyanide.

5. The process of claim 1 wherein said cyano compound is hydrocyanic acid.

6. The process of claim 1 wherein said cyano compound is metal cyanide which is an alkali metal cyanide.

7. The process of claim 6 wherein said alkali metal cyanide is selected from sodium cyanide and potassium cyanide.

8. The process of claim 1 wherein said (2,3-epoxypropyl)-trimethylammonium halide is (2,3-epoxypropyl)trimethylammonium chloride, said cyano compound is a metal cyanide which is an alkali metal cyanide.

9. The process of claim 1 wherein said (2,3-epoxypropyl)-trimethylammonium halide is (2,3-epoxypropyl)trimethylammonium chloride, said cyano compound is a metal cyanide and said metal cyanide is sodium cyanide.

10. The process of claim 1 wherein said (2,3-epoxypropyl)-trimethylammonium halide is (2,3-epoxypropyl)trimethylammonium chloride, said cyano compound is hydrocyanic acid and said reaction is further characterized by being carried out in the presence of a catalytic amount of an alkali metal cyanide.

* * * * *

UNITED STATES PATENT OFFICE
CERTIFICATE OF CORRECTION

PATENT NO. : 4,070,394
DATED : January 24, 1978
INVENTOR(S) : Karl E. Wiegand

It is certified that error appears in the above-identified patent and that said Letters Patent are hereby corrected as shown below:

Column 3, line 68, after "cyanide," insert
-- cuprous and cupric cyanide, cobaltous cyanide, zinc cyanide,--

Signed and Sealed this

Fourth Day of July 1978

[SEAL]

Attest:

RUTH C. MASON
Attesting Officer

DONALD W. BANNER
Commissioner of Patents and Trademarks